United States Patent
Charng

(12) 
(10) Patent No.: US 6,369,297 B1
(45) Date of Patent: Apr. 9, 2002

(54) INDUCIBLE ONE-COMPONENT PLANT GENE TAGGING

(75) Inventor: Yuh-Chyang Charng, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/585,094

(22) Filed: Jun. 1, 2000

(51) Int. Cl.$^7$ .............. A01H 1/00; A01H 5/00; C12N 5/04; C12N 15/82
(52) U.S. Cl. .............. 800/291; 800/266; 800/270; 800/298; 435/419; 435/468
(58) Field of Search .................. 800/278, 298, 800/291, 266, 270; 536/23.1; 435/468, 410, 419

(56) References Cited

U.S. PATENT DOCUMENTS 5,013,658 A * 5/1991 Dooner et al. ............ 435/172.3

OTHER PUBLICATIONS

Charng, et al, " A 200–bp constructed inducible PR–1a promoter fusion to the Ac transposase . . . ", 1997, Plant Science, vol. 130 pp. 73–86.*

Charng, et al, "Fusion of the inducible promoter of the PR–1a gene to the Activator transposase gene can transactive excision of non–atonomous . . . ", 1995, Plant Science vol. 106 pp. 141–155.*

Jones et al., "Visual Detection . . . ," Science, 244:204–207, 1989.

Finnegan et al., "Transposable Elements . . . ," The Plant Cell, 1:757–764, 1989.

Baker et al., "Phenotypic assay . . . ," The EMBO Journal, 6:1547–1554, 1987.

Charng et al., "The firefly luciferase . . . ," Plant Science, 98:175–183, 1994.

Charng et al., "Fusion of the inducible . . . ," Plant Science, 106:141–155, 1995.

* cited by examiner

*Primary Examiner*—Elizabeth F. McElwain
*Assistant Examiner*—Cynthia Collins
(74) *Attorney, Agent, or Firm*—Fish & Richardson P.C.

(57) ABSTRACT

A nucleic acid including (1) an inducible transposable element having a first nucleotide sequence encoding a transposase, and an inducible promoter operably linked to the first nucleotide sequence; (2) an uncoupled promoter; and (3) a second nucleotide sequence encoding a polypeptide such that, upon removal of the inducible transposable element during transposition, the uncoupled promoter becomes operably linked to the second nucleotide sequence.

7 Claims, No Drawings

INDUCIBLE ONE-COMPONENT PLANT GENE TAGGING

BACKGROUND OF THE INVENTION

Transposable elements are powerful genetic tools for the cloning of genes on the basis of their phenotypes (Bingham et al., Cell 25:693–704, 1981). Introduction of the maize transposon Activator (Ac) into heterologous plant species has resulted in the isolation of various genes by transposon tagging. See, e.g., Aarts et al., Nature 363:715–717, 1993; Jones et al., Science 266:789–793, 1994; and Whitham et al., Cell 78:1101–1115, 1994. The use of an autonomous Ac element for gene tagging allows one to take advantage of the higher transposition activity of Ac associated with the homozygous state, and thereby to increase the possibility of insertion into a target gene.

SUMMARY OF THE INVENTION

The invention relates to the discovery of a transposition system requiring only a single inducible genetic component and that can be used for plant gene tagging in germinal tissue. The genetic component generally contains a promoter separated from an open reading frame (ORF) by an inducible transposable element. Transposition is then monitored by determining whether the protein encoded by the open reading frame is present in the plant or cell thereof.

Accordingly, the invention features a nucleic acid containing (1) an inducible transposable element including a first nucleotide sequence encoding a transposase (e.g., the transposase of a maize transposable element Activator) and an inducible promoter (e.g., a pathogenesis-related protein 1a promoter [PR-1a promoter; see Grüner et al., Eur. J. Biochem. 220:247–255, 1994]) operably linked to the first nucleotide sequence; (2) an uncoupled promoter (e.g., a 1' promoter of a T-DNA 1' gene); and (3) a second nucleotide sequence encoding a polypeptide (e.g., a detectable protein, such as luciferase). Upon removal of the inducible transposable element during transposition, the uncoupled promoter becomes operably linked to the second nucleotide sequence. The inducible transposable element can further include a selectable marker gene (e.g., one that expresses a hygromycin phosphotransferase).

The invention also includes a transgenic plant containing a nucleic acid of the invention, and a method of producing a progeny plant containing a transposition by (1) contacting a germinal tissue of a transgenic plant of the invention with an inducer (e.g., a chemical inducer) of the inducible promoter, (2) pollinating the germinal tissue, and (3) germinating seedlings from the transgenic plant to produce the progeny plant. A "germinal tissue" is any tissue that can give rise to an entire progeny plant, such as a flower tissue (e.g., the pollen, pollen mother, egg, or egg mother cells of the flower) or precursor tissues thereof. If the inducible promoter is a PR-1a promoter, then the inducer can be an aqueous solution containing at least about 0.5 mM (e.g., about 1 to 10 mM, about 5 mM, at least about 30 mM, and about 50 mM) salicylic acid.

By one genetic element being "operably linked" to another is meant that a genetic element (either in a plus strand, minus strand, or double stranded form) is structurally configured to operate or affect another genetic element. For example, a promoter operably linked to a sequence encoding a polypeptide means that the promoter initiates transcription of a nucleic acid encoding the polypeptide. An "uncoupled promoter" means that a promoter is not operably linked to a particular genetic element. A "selectable marker gene" is a gene that expresses a nucleic acid or protein which confers a readily observable (by any means known in the art) phenotype in a cell or plant harboring the marker gene. A "detectable protein" is a protein that is readily observable using any known means in the art of molecular biology, such as by fluorescence, phosphorescence, luminescence, radioactivity, enzymatic activity, or chromogenic activity.

The nucleic acids, transgenic plants, and methods described above are useful for generating mutated transgenic plants by inducing transposon insertion in germinal tissue. These mutants can then be screened for particular phenotypes. An examination of the site of insertion in these mutants can help identify a gene that is involved in the particular phenotype.

Other features or advantages of the present invention will be apparent from the following detailed description, and also from the claims.

DETAILED DESCRIPTION

The invention is based on a single nucleic acid construct which, after integration into a plant genome using standard methods, can be used to induce a transposition from one position in a genome to another in a germ line cell. The transposition is observable upon removal of the transposon from its site in the construct, the removal bringing together a previously uncoupled promoter and an ORF that expresses, e.g., a detectable protein.

Without further elaboration, it is believed that one skilled in the art can, based on the above disclosure and the description below, utilize the present invention to its fullest extent. The following example is to be construed as merely illustrative of how one skilled in the art can isolate and use the invention, and are not limitative of the remainder of the disclosure in any way. Any publications cited in this disclosure are hereby incorporated by reference.

EXAMPLE

Materials and Methods

DNA manipulation. In general, recombinant DNA techniques were performed as described in Sambrook et al., Molecular Cloning: A Laboratory Manual., Cold Spring Harbor Laboratory Press, Cold Spring Harbor, N.Y., 1989. The materials and methods required for construction of the plasmids pBinLucAc1, pPCVPR, and pBinHygTs are described in Charng et al., Plant Sci. 106:141–155, 1995.

To ensure efficient excision for this transposable element, most of the nonessential regions of Ac was removed to make room for an inducible transposase and a hygromycin resistance gene. A 1.7 kb Hind III-Eco RI fragment of pPCVPR containing the PR-1a promoter and a poly(A) fragment (Ag7) was inserted into the Hind III-Eco RI site of pUC19, yielding pAgRP. The 5' end of Ac was obtained directly from the plasmid pKU3 (Baker et al., EMBO J. 6:1547–1554, 1987) after digestion with Eco RI. A 3 kb Eco RI fragment of pKU3 containing the 1' promoter and the 5' region of Ac was inserted into the Eco RI site of pAgRP, giving rise to p1'AcRp. The transposase gene was isolated from pBinHygTs as a 2.6 kb Bam HI fragment and was inserted into the Bam HI site of p1'AcRp, yielding p1'AsTRP. The 5' nonessential regions of Ac were removed by partial digestion of p1'AsTRP with Bsp EI and Eco RI and subsequent self-ligation, giving rise to p1'AsTRPAΔ. A 5.2 kb Hind III-Eco RI fragment of p1'AsTRPAΔ was then inserted into the binary vector Bin19 (Bevan, Nucleic Acids Res. 12:8711–8721, 1984) that had been digested with the same two enzymes. This procedure yielded pBin1'AsTRPΔ, which contains an inducible transposase (PR-1a::TPase), 400 bp of the 5' end of Ac, and the 1' promoter.

For construction of a luciferase (LUC) gene (Ow et al., Science 234:856–859, 1986) that flanks the 3' end of the transposable element fused to a hygromycin phosphotransferase (HPT) gene, pPCV720 (Koncz et al., Mol. Gen. Genet. 204:383–396, 1986) was first digested with Eco RI and Sph I to obtain a 1.4 kb fragment that contained a portion of the hygromycin resistance gene. This fragment was ligated to pUC19 which had also been digested with Eco RI and Sph I, yielding pHyg. This latter plasmid was then digested with Kpn I, rendered blunt-ended with T4 DNA polymerase, and ligated with a 2.2 kb Sac I-Acc I fragment of pBinLucAc1, which was also rendered blunt-ended with T4 polymerase. This procedure yielded pLucAcHyg, which contains the 3' end of the Ac element directly flanking the 3' end of the HPT gene. The plasmid pLucAcHyg was then digested with Pst I and ligated with the 3.4 kb Pst I fragment of pPCVPR, producing pLucAcHygPR. This latter plasmid contains the LUC gene flanking the 3' end of the Ac element (~370 bp), the complete HPT gene, the PR-1a promoter, and the Ag7 fragment.

To construct an inducible transposable element that contains an inducible transposase gene and a hygromycin resistance gene inserted in the 5' untranslated region of the LUC gene in the binary vector Bin19, the following three fragments were generated and ligated: (i) a 4.3 kb Pst I-Sph I fragment of Bin19, (ii) a 10 kb fragment of pBin1'AsTRPΔ obtained after digestion with Hind III (partially) and Pst I, and (iii) a 4.6 kb fragment of pLucAcHygPR obtained after digestion with Sph I (partially) and Hind III. This procedure yielded the plasmid pINAc, which is 18.9 kb in size and contains the 7.2 kb artificial inducible transposable element INAc.

Plant transformation. All transformations were performed with tobacco and tomato, and the transgenic plants were regenerated as described in Charng et al., Plant Sci. 98:175–183, 1994; and Charng et al., Plant Sci. 106:141–155, 1995.

Assay of reporter gene activities. Luciferase activity was determined as described in Howell et al., "Use of the firefly luciferase gene as a reporter of gene expression in plants," In: Gelvin et al., eds, *Plant Molecular Biology Manual*, pp. B8/1–B8/11, Kluwer Academic Publishers, Dordrecht, 1989; using a Lumat LB 9501 luminometer (Berthold, Munich, Germany). For imaging of luciferase activity, hygromycin-resistant (Hyg$^R$) seedlings were sprayed with luciferin, incubated in the dark for 5 minutes, and then placed under a charge-coupled device camera (ChemiImager 4000; Alpha Innotech, San Leandro, Calif.) for detection of luminescence. Image acquisition and processing were performed with AlphaEase software (Alpha Innotech). Exposure time was 30 minutes.

Isolation of genomic DNA. Genomic DNA was isolated from transformed plants with the use of a kit (BIO 101, Vista, Calif.). In brief, fresh leaves (2 g) or callus tissue (0.1 g) was frozen in liquid nitrogen in a mortar and ground with a pestle. Nuclei were isolated and lysed by protease treatment, and genomic DNA was precipitated with ethanol and dissolved in TE buffer (10 mM Tris-HCl, 1 mM EDTA; pH 8.0).

PCR analysis of INAc excision events. Transposition of INAc from the INAc::LUC construct in transgenic plants was analyzed by the polymerase chain reaction (PCR) with three oligonucleotide primers: primer 1' (identical to the T-DNA promoter sequence from position 352 to 370 as numbered by Velten et al., EMBO J. 3:2723–2730, 1984; 5'-CTTACGTCACGTCTTGCGC-3', SEQ ID NO:1), primer LUC (complementary to the luciferase coding sequence from position 577 to 556 as numbered by De Wet et al., Mol. Cell Biol. 7:725–737, 1987; 5'-CGGGAGGTAGATGAGATGTGAC-3', SEQ ID NO:2), and primer AC4 (complementary to the Ac sequence from position 1017 to 996 as numbered by Müller-Neumann et al., Mol. Gen. Genet. 198:19–24, 1984; 5'-TGGTGATCTCGAGGTG CTAGAC-3', SEQ ID NO:3). Each reaction mixture contained ~0.1 µg of template DNA, 0.25 µg of each primer, 0.2 mM deoxynucleoside triphosphates, 1 U of Taq DNA polymerase, 10 mM Tris-HCl (pH 8.3), 50 mM KCl, 1.5 mM MgCl$_2$, and 0.01% (w/v) gelatin. The amplification protocol was 30 cycles of 1 minute at 94° C., 2 minutes at 55° C., and 2 minutes at 72° C., and was performed in a MiniCycler (MJ Research, Watertown, Mass.).

Results

Construction of the INAc element. A PR-1a::TPase fusion and an HPT gene were inserted between ~400 bp fragments of each end of the Ac element. The orientation of the PR-1a::TPase fusion is opposite to that of the native transposase of the Ac element in order to eliminate triggering of the transposase by the Ac promoter. The INAc element was inserted between the T-DNA 1' promoter and the coding region of the LUC gene in the binary vector Bin19, yielding the plasmid pINAc. Activity of the LUC reporter gene was restored after excision of INAc.

The pINAc plasmid was introduced into the *Agrobacterium tumefaciens* strain LBA4404 to transform tobacco and tomato. Twenty-five transformed tobacco plants were regenerated from 14 independent calli, and nine transformed tomato plants were regenerated from nine independent calli. These transgenic plants were used for the induction and detection of transposition events.

Spontaneous transposition of INAc in shoots derived from primary transformed calli. To determine whether INAc undergoes spontaneous transposition, luciferase activity was assayed in the primary regenerated shoots of tobacco and tomato transformants. A high frequency of LUC$^+$ shoots was apparent among tomato transformants, as shown in Table 1.

TABLE 1

| Tobacco | Luciferase activity (RLU/µg of total protein) | Tomato | Luciferase activity (RLU/µg of total protein) |
| --- | --- | --- | --- |
| Samsun | 4.3 | Moneymaker | 3.3 |
| IA1 | 7 | MA1 | 1286 |
| IA2 | 12.8 | MB1 | 19.3 |
| IA3 | 21.4 | MC1 | 714 |
| IB1 | 7.5 | MD1 | 1643 |
| IC1 | 5.7 | ME1 | 30 |
| IC2 | 10.7 | MF1 | 40 |
| IC3 | 6.4 | MG1 | 25 |
| ID1 | 15.7 | MH1 | 11 |
| IF1 | 1214 | MI1 | 1731 |
| IF2 | 6.4 | | |
| IK1 | 1643 | | |
| IK2 | 778 | | |
| IK3 | 786 | | |
| IM1 | 32 | | |
| IM2 | 9.8 | | |
| IN1 | 17 | | |
| IN2 | 8.5 | | |
| IO1 | 9.2 | | |
| IP1 | 11 | | |
| IP2 | 9 | | |
| IR1 | 10.5 | | |
| IS1 | 601 | | |

TABLE 1-continued

| Tobacco | Luciferase activity (RLU/µg of total protein) | Tomato | Luciferase activity (RLU/µg of total protein) |
|---|---|---|---|
| IS2 | 30 | | |
| IT1 | 7.5 | | |
| IU1 | 12.1 | | |

Luciferase activity was measured in shoots of untransformed tobacco (Samsun) and tomato (Moneymaker) plants, as well as in those of primary transformants. Activity was expressed in relative light units (emission was measured for 2 seconds) per microgram of total protein. Values of less than 50 RLU per milligram corresponded to the absence of luciferase activity. Plants regenerated from the same callus contained the same two letters in their designation.

Four out of nine independent transformed tomato shoots (MA1, MC1, MD1, and MI1) exhibited luciferase activity. Among the transformed tobacco plants, three transformants regenerated from one callus (IK) exhibited luciferase activity, as did one of two regenerated shoots derived from each of two other calli (IF and IS). Luciferase activity was not detected in the remaining 20 tobacco shoots regenerated from 11 independent calli (IA, IB, IC, ID, IM, IN, IO, IP, IR, IT, and IU).

To verify that the observed reporter gene activities were due to excision of the INAc element, genomic DNA from LUC+ plants was analyzed by PCR using the primers LUC (complementary to the luciferase coding sequence), AC4 (complementary to the Ac sequence), and 1' (identical to a region of the 1' promoter). With the primers 1' and AC4, a 0.9 kb PCR product was obtained with DNA from LUC− tissue of either transformed tobacco plant IP1 or transformed tomato plant MH1. In contrast, no PCR product was generated from genomic DNA of these transformants with primers 1' and LUC. The distance between these two primers was 8.0 kb in the intact INAc::LUC chimeric gene construct. Together, these results indicated that the INAc element had not undergone transposition in LUC− tissue. In contrast, primers 1' and LUC generated a 0.7 kb PCR product with genomic DNA from LUC+ tissue of either the transformed tobacco plant IK1 or the transformed tomato plant MI1. In the presence of all three primers and genomic DNA from LUC+ tissue yielded PCR products of 0.7 and 0.9 kb, indicating that the LUC+ tissue contained both cells in which INAc had undergone transposition and cells in which it had not.

Induction of INAc transposition. Given the high frequency of spontaneous INAc transposition in tomato and the low number of shoots regenerated from tomato calli, the induction of INAc transposition by salicylic acid (SA) in transgenic tobacco calli and plants was studied. The effect of SA on INAc transposition was determined by incubating Hyg$^R$ calli with a diameter of 0.5 to 1 cm for various times on callus regeneration medium containing either 0.1 or 1 mM SA. The calli for the transformed lines IA, IC, and IK were directly divided from the primary regenerated calli, which were large and generated many primary transformed shoots. For transformed lines IF, IM, IN, IP, and IR, the calli were obtained from the primary transformants IF1, IM1, IN1, IP1, and IR1. Leaf disks were excised and incubated on callus regeneration medium to yield enough calli for induction experiments. The calli were treated with 0.1 mM SA for 60 days, or were incubated with 1 mM SA for 10 days and then transferred to normal callus regeneration medium for an additional 50 days. As a control, calli were incubated on normal callus regeneration medium for 60 days. Luciferase activity was measured in the shoots that developed from the calli during incubation and was expressed as −, +, ++, or +++ as described in Table 2.

TABLE 2

| Callus Induction | IA | IC | IF[1] | IK[1] | IM1 | IN1 | IP1 | IR1 |
|---|---|---|---|---|---|---|---|---|
| no SA | 3−[2] | 2− | 2++ | 3++ | 4−[2] 1+ | 8−[2] 1+ | 7−[2] | 3− |
| 0.1 mM SA (60 days) | 2+ 2++ | 5− | 5++ | 8++ 1+++ | 4− 8+ | 2− 8+ 1++ | 1− 4+ | 3+ 5++ |
| 1 mM SA (10 days) | 6− 2+ 4++ 1+++ | 12− | 3++ | 12++ 4+++ | 9− 2+ 1+++ | 7− 2+ | 1− 3+ 7++ 1+++ (IP3) | 8− 3+ 1++ |

[1]Transformed tobacco lines that exhibited spontaneous transposition events (see Table 1).
[2]Several shoots were selected for floral induction experiments. IP3 indicated the transformed line that yielded high luciferase activity after induction and that was used for PCR analysis.

The numerical values in Table 2 indicate the number of LUC+ shoots that were regenerated from SA-treated tobacco calli. Symbols denoting the amount of luciferase activity (RLU per microgram of total protein) are as follows: (−) <50 (with no typical luciferase activity kinetics); (+) 50 to 500 RLU; (++) 500 to 5000 RLU; and (+++) >5000 RLU. Based on previous studies (Charng et al., Plant Sci. 98:175–183, 1994; and Charng et al., Plant Sci. 106:141–155, 1995), (+) most likely corresponded to the occurrence of transposition in only a few cells, (++) most likely indicated that transposition had occurred in portions of the shoot, and (+++) most likely represented transposition events throughout the entire shoot.

SA at a concentration of 0.1 mM was sufficient to induce the expression of PR-1a::TPase, thereby inducing transposition events. In transformed lines IA and IP1, high transposition frequencies were observed in shoots regenerated from the SA-treated calli, whereas luciferase activity was not detected in shoots derived from untreated calli. Eleven out of 17 shoots from SA-treated IA calli and 15 out of 17 shoots from SA-treated IP calli exhibited luciferase activity. The induced transposition of INAc was confirmed by PCR analysis of genomic DNA from the transformed shoot IP3, which yielded the highest level of luciferase activity after SA induction. For transformed lines IM1, IN1, and IR1, transposition at various levels of efficiency was also detected in shoots derived from SA-treated calli (11 out of 24 shoots for IM1, 11 out of 20 shoots for IN1, and 12 out of 20 shoots for IR1). One of the untreated calli of each of the transformed lines IM1 and IN1 yielded luciferase activity characterized as low (+). For the transformed line IK, the luciferase activities of induced shoots were slightly higher than those of uninduced shoots. Finally, luciferase activity was not detected in the shoots regenerated from transformed callus IC in the absence or presence of SA, although luciferase activity was detected in the nodes of the adult transformed plant IC3, indicating that this line contains a functional INAc element.

After induction with 0.1 mM SA, luciferase activity was detected in 33 out of 45 shoots (73%) regenerated from the transformed lines IA, IC, IM1, IN1, IP1, and IR1. A lower transposition frequency, 27 out of 70 shoots (39%), was apparent for these transformed lines incubated with 1 mM SA. However, higher luciferase activities were observed in independent LUC+ shoots regenerated from calli in the presence of 1 mM SA. Thus, whereas only two out of nine shoots (22%) from IA and IP1 calli exhibited medium (++) luciferase activity in response to induction with 0.1 mM SA, 13 out of 25 shoots (52%) exhibited medium (++) or high (+++) luciferase activity in response to 1 mM SA. For the transformed line IK, which exhibited medium luciferase activity in uninduced tissue, 4 out of 16 shoots (25%) exhibited high luciferase activity in response to induction with 1 mM SA, compared with a value of 1 out of 9 shoots (11%) after induction with 0.1 mM SA. These results suggested that a greater number of early transposition events were triggered by 1 mM SA than by 0.1 mM SA.

Analysis of SA-induced transposition in R1 progeny of transformed tobacco plants. An important feature of an inducible transposable element is its susceptibility to induced transposition in germinal tissue. Such susceptibility markedly increases the probability of success of transposon tagging in the isolation of important plant genes. To determine the effectiveness of INAc for gene tagging, the induction of transposition in germ-line tissue was studied using 14 transformed tobacco plants from lines IA, IM, IN, and IP. These plants were regenerated from calli in the absence of SA and did not exhibit luciferase activity (Table 2). The flowering tissues of plants were sprayed with SA at concentrations of 50, 5, or 1 mM, and after 2 hours these tissues were watered to remove SA. Exposure to 50 mM SA resulted in a marked decrease in the frequency of fruiting and yielded only a few mature capsules. The R1 progeny was analyzed by comparing the germination frequency apparent on normal germination medium with that observed on germination medium containing hygromycin B, as summarized in Table 3.

TABLE 3

| Plant (treatment) | | Hygromycin B (30 mg ml$^{-1}$) | | Normal medium |
|---|---|---|---|---|
| | | Germ. Seedlings Capsule/total seeds | LUC assay[1] | Germ. seedlings /total seeds |
| IA3 (none) | A | 66/86 (76%) | 5+/50 | 86/92 (93%) |
| IM3 (none) | A | 88/117 (75%) | 3+/50 | 105/113 (93%) |
| IN3 (none) | A | 75/103 (73%) | 0/50 | 98/112 (88%) |
| IP8 (none) | A | 38/56 (68%) | 0/38 | 135/150 (90%) |
| IA7 (1 mM SA) | A | 56/138 (41%) | 22+/56 | 97/121 (80%) |
| | B | 49/127 (39%) | 6+/49 | 85/104 (82%) |
| | C | 62/108 (57%) | 18+, 1+++/50 | 91/107 (85%) |
| | D | 65/124 (52%) | 24+/51 | 90/112 (80%) |
| | E | 36/87 (41%) | 8+/36 | 99/111 (89%) |
| IM4 (1 mM SA) | A | 81/118 (68%) | 2+/52 | 104/117 (89%) |
| | B | 66/94 (70%) | 6+/56 | 105/128 (82%) |
| | C | 80/109 (73%) | 9+/50 | 102/113 (90%) |
| | D | 78/121 (64%) | 7+, 1+++/52 | 94/101 (93%) |
| | E | 54/89 (60%) | 4+/54 | 101/131 (77%) |
| IN3 (1 mM SA) | A | 79/106 (75%) | 0/50 | 101/107 (94%) |
| | B | 81/111 (73%) | 1+/48 | 115/124 (93%) |
| | C | 65/85 (76%) | 0/55 | 100/119 (84%) |
| | D | 78/108 (72%) | 9+/51 | 104/108 (96%) |
| | E | 85/121 (70%) | 12+/50 | 91/95 (96%) |
| IP5 (1 mM SA) | A | 100/182 (55%) | 28+/53 | 100/117 (85%) |
| | B | 89/118 (75%) | 32+/50 | 105/125 (84%) |
| | C | 80/133 (60%) | 30+/52 | 101/113 (89%) |
| | D | 98/165 (59%) | 32+/52 | 94/108 (87%) |
| | E | 108/141 (77%) | 40+/54 | 111/135 (82%) |
| IA6 (5 mM SA) | A | 95/125 (76%) | 28+/46 | 103/117 (88%) |
| | B | 79/122 (65%) | 24+/52 | 89/102 (87%) |
| | C | 92/138 (66%) | 29+, 1+++/50 | 108/125 (86%) |
| | D | 73/99 (74%) | 33+/50 | 94/101 (93%) |
| | E | 100/133 (75%) | 35+/50 | 90/98 (92%) |
| 1M5 (5 mM SA) | A | 75/135 (55%) | 19+/50 | 107/117 (91%) |
| | B | 63/101 (62%) | 15+, 1+++/50 | 106/115 (92%) |
| | C | 52/98 (53%) | 30+152 | 109/123 (89%) |
| | D | 50/132 (38%) | 29+/50 | 106/118 (90%) |
| | E | 83/119 (70%) | 18+, 1+++/50 | 101/125 (81%) |
| IN4 (5 mM SA) | A | 83/113 (73%) | 12+/50 | 97/108 (90%) |
| | B | 75/106 (71%) | 0/50 | 113/125 (90%) |
| | C | 89/124 (72%) | 12+/50 | 110/118 (93%) |
| | D | 85/112 (76%) | 11+/50 | 105/128 (82%) |
| | E | 68/95 (72%) | 4+/52 | 121/135 (90%) |
| IP9 (5 mM SA) | A | 80/156 (51%) | 20+/42 | 177/187 (95%) |
| | B | 131/208 (63%) | 42+, 3+++/50[2] | 185/225 (82%) |
| | C | 82/124 (66%) | 30+/50 | 190/213 (89%) |
| | D | 78/186 (42%) | 32+/52 | 164/198 (83%) |
| | E | 130/222 (59%) | 40+, 1+++/54 | 201/245 (82%) |
| IA5 (50 mM SA) | A | 2/216 (0.9%) | 1+/2 | 1/117 (0.85%) |
| | B | 100/172 (58%) | 6+/12 | 39/92 (42%) |
| | C | 12/108 (11%) | 10+, 1+++/12 | 9/65 (14%) |
| | D | 1/240 (0.4%) | 1+/1 | 4/71 (6%) |
| IP6 (50 mM SA) | A | 0/38 (0%) | | 0/50 (0%) |
| | B | 0/56 (0%) | | 0/71 (0%) |
| | C | 1/43 (0.2%) | 1+/1 | 2/35 (6%) |
| | D | 4/98 (0.4%) | 4+/4 | 5/78 (6%) |
| | E | 0/2 (0%) | | 0/3 (0%) |

[1]The proportion of LUC$^+$ seedlings after selection on hygromycin B and the luciferase activity are indicated as in Table 2.
[2]An additional 152 Hyg ® seedlings from this capsule were analyzed subsequently as described in the text.

Table 3 shows the germination frequency of the R1 progeny obtained from individual self-pollinated capsules derived from control or SA-treated transformed tobacco plants. Capsules are designated A through E.

A marked variability in germination frequency was apparent for capsules of tobacco plants IA5 and IP6 exposed to 50 mM SA. However, the germination frequency of the progeny from each capsule on medium containing hygromycin B was similar to that apparent on normal medium. These results suggest that the low germination frequencies of the R1 progeny of transgenic plants IA5 and IP6 were largely due to the high concentration of SA.

The proportion of LUC$^+$ seedlings after selection with hygromycin B was next determined. With the exception of the transformed lines with low germination frequencies (IA5 and IP6), ~50 Hyg$^R$ seedlings from each capsule were assayed for luciferase activity. A large proportion of LUC$^+$ seedlings was apparent for transformed plants treated with SA (Table 3). Thus, for the transformed plants exposed to SA (1, 5 or 50 mM), 785 out of 2053 seedlings (38%) exhibited luciferase activity, with 10 seedlings showing high activity. In contrast, for transformed plants not treated with SA, 8 out of 267 seedlings (3%) exhibited low luciferase activity. Although SA-treated transformed plants yielded a high proportion of LUC$^+$ seedlings, most such seedlings exhibited low luciferase activity. These results indicated that transposition of INAc occurred frequently in embryonic tissues but with variable efficiency.

The data shown in Table 3 were then analyzed for the effect of SA concentration. For transformed plants treated with 1 mM SA, 291 out of 1021 seedlings (29%) exhibited luciferase activity, with 2 seedlings showing high activity. For the transformed plants exposed to 5 mM SA, 470 out of 1000 seedlings (47%) exhibited luciferase activity, with 7 seedlings showing high activity. For the transformed plants treated with 50 mM SA, 24 out of 32 seedlings (75%) exhibited luciferase activity, with 1 seedling showing high activity. These results suggested that SA increases the frequency of production of LUC$^+$ seedlings in a dose-dependent manner, although, as mentioned above, treatment of plants with 50 mM SA resulted in a marked decrease in the frequency of fruiting.

Given that the high luciferase activity in a seedling likely results from transposition of the INAc element in germinal tissue or during the early stages of embryogenesis, the efficiency of INAc transposition for each concentration of SA was determined on the basis of the frequency of seedlings exhibiting high luciferase activity. With this approach, the efficiency of INAc transposition was determined to be 0.2, 0.7, and 3.1% for transformed plants treated with 1, 5, and 50 mM SA, respectively, as shown in Table 4.

TABLE 4

| | Treatment | | | | | | | | | |
|---|---|---|---|---|---|---|---|---|---|---|
| | None | | 1 mM SA | | 5 mM SA | | 50 mM SA | | Mean | |
| Plant | S$^1$ | G$^2$ | S | G | S | G | S | G | S | G |
| IA | 10 | 0 | 33 | 0.4 | 60 | 0.4 | 70 | 3.7 | 45 | 0.5 |
| IM | 6 | 0 | 11 | 0.4 | 45 | 0.8 | | | 25 | 0.5 |
| IN | 0 | 0 | 9 | 0 | 15 | 0 | | | 11 | 0 |
| IP | 0 | 0 | 62 | 0 | 68 | 1.6 | 100 | 0 | 61 | 0.7 |
| Mean | 4 | 0 | 29 | 0.2 | 47 | 0.7 | 75 | 3.1 | | |

[1]Percentage of Hyg ® progeny that were LUC$^{+.}$
[2]Percentage of Hyg ® progeny that exhibited high luciferase activity.

The numerical values in Table 4 are the transposition efficiencies (%) of INAc derived from the data shown in Table 3.

The results were then analyzed taking into account the fact that all transformed plants listed in Table 3 were regenerated from four independent calli. The frequencies of Luc$^+$ seedlings produced by transformed plants derived from the different regenerating calli were 45% (253 LUC$^+$ seedlings out of 566 seedlings), 25% (144/566), 11% (61/556), and 61% (335/552) for lines IA, IM, IN, and IP, respectively (Table 4). The germinal transposition efficiencies based on the frequency of seedlings exhibiting high luciferase activity were 0.5, 0.5, 0, and 0.7% for the transformed lines IA, IM, IN, and IP, respectively. Seedlings with a high luciferase activity were produced by the independent transformed plants IA7 (1 mM SA), IM4 (1 mM SA), IA6 (5 mM SA), IM5 (5 mM SA), IP9 (5 mM SA), and IA5 (50 mM SA) at frequencies of 0.4, 0.4, 0.4, 0.8, 1.6, and 3.7%, respectively.

Given that capsule B of the transformed plant IP9 yielded the highest frequency of seedlings with a high luciferase activity, the remainder of the progeny of this capsule was analyzed. An additional 152 Hyg$^R$ seedlings were obtained for luciferase activity screening. Three of the assayed 50 Hyg$^R$ seedlings exhibited a complete bioluminescence image. This nondestructive detection method identified a total of nine additional seedlings with high luciferase activity. These seedlings were subsequently subjected to Southern blot analysis. Thus, a total of 12 out of 202 Hyg$^R$ seedlings from capsule B of transformed plant IP9 exhibited high luciferase activity.

To characterize the germinal transposition events, Southern blot analysis was performed on Pst I-digested genomic DNA from Hyg$^R$ progeny (LUC$^+$ or LUC$^-$) of SA-treated transformed tobacco lines IA, IM, and IP, using probes consisting of a 2.6 kb Bam HI fragment of the transposase gene and a 1.6 kb Bam HI-Hind III fragment of the PR-1a promoter. All capsules that yielded progeny with high luciferase activity were examined, including 36 progeny from capsule C of IA7 (termed A7C01 to A7C36), 36 progeny from capsule C of IA6 (A6C01 to A6C36), 18 progeny from capsule D of IM4 (M4D01 to M4D18), 18 progeny from capsule B of IM5 (M5B01 to M5B18), 36 progeny from capsule E of IM5 (M5E01 to M5E36), 36 progeny from capsule B of IP9 (P9B01 to P9B36), 36 progeny from capsule E of IP9 (P9E01 to P9E36), and 12 progeny from capsule C of IA5 (A5C01 to A5C12). All progeny of the 50 mM SA-treated plant IP6 (P6C01 and P6D01 to P6D04) were also analyzed. The uninduced transformed plants IA3, IM3, and IP8 yielded hybridizing fragments of 6.5 kb, 7 kb, and 8 kb, respectively, corresponding to the primary sites of INAc integration. Additional bands of various sizes but larger than 5.6 kb is indicative of transposition and were detected in plants A7C29 (7 kb), A6C08 (7.2 kb), M4D17 (7.7 kb), M5B08 (8 kb), M5E35 (8.4 kb), and P9E20 (10 kb), all of which exhibited high luciferase activity. The transformed plants P9B01 to P9B09, all of which were shown to possess high luciferase activity, yielded hybridizing fragments of 8.5, 12, 7.5, 9.5, 10, 6.5, 9, 13, and 10 kb, respectively. A band corresponding to the primary site of INac integration was not detected. Transformed plant P9B29, which did not exhibit luciferase activity, yielded a band of 9.2 kb. These results indicated the occurrence of induced transposition of the INAc element in floral tissues of SA-treated transformed tobacco plants. The transformed plant A5C04 exhibited high luciferase activity and yielded two hybridizing bands of 21 and 14 kb but no band corresponding to the primary site. The intensity of the 14 kb band was much less than that of the 21 kb band. These observations indicated that plant A5C04 contains two transposed INAc elements, one of which (corresponding to the 14 kb band) was present in only a small proportion of cells.

Other inducers. Given that 5-azacytidine was recently shown to enhance Ac excision in transformed plants (Scortecci et al., Plant Cell Physiol. 38:336–343, 1997), the use of this agent was examined as a second inducer to trigger transposition events in tobacco seedlings harboring INAc. Combined treatment with 0.1 mM 5-azacytidine and 1 mM SA resulted in a higher transposition efficiency than that obtained by treatment with SA alone.

Summary. The percentages of HygR seedlings that were $LUC^+$ were 29, 47, and 75%, and the percentages of $Hyg^R$ seedlings that exhibited high luciferase activity were 0.2, 0.7, and 3.1% for plants treated with SA at concentrations of 1, 5, and 50 mM, respectively (Table 4). These observations indicated that SA increases the frequency of transposition events in floral tissues in a dose-dependent manner. All transformed tobacco plants used for the floral induction experiments were derived from four independent regeneration calli. The percentages of HygR seedlings that were $LUC^+$ were 45, 25, 11, and 61% for the transformed lines IA, IM, IN, and IP, respectively. Thus, the location of the INAc element in the plant genome also appears to contribute to the efficiency of transposition.

The results described herein provide an illustrative example of the nucleic acids, transgenic plants, and methods of the invention.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

For example, while the inducible promoter described herein is induced by a chemical inducer compound, other inducible promoters (e.g., heat shock protein promoters) that are induced by physical conditions (e.g., heat) can be used in the invention.

What is claimed is:

1. A method of producing a progeny plant containing a transposition, the method comprising:

providing a transgenic plant containing a nucleic acid that includes:

an inducible transposable element including a first nucleotide sequence encoding a transposase, and an inducible promoter operably linked to the first nucleotide sequence;

an uncoupled promoter; and a second nucleotide sequence encoding a polypeptide, wherein, upon removal of the inducible transposable element during transposition, the uncoupled promoter becomes operably linked to the second nucleotide sequence;

contacting a flowering tissue of the transgenic plant with an inducer of the inducible promoter to thereby induce a transposition in a germ cell of the transgenic plant;

pollinating the germinal tissue of the transgenic plant; and germinating seedlings from the germinal tissue to produce the progeny plant.

2. A method of producing a progeny plant containing a transposition, the method comprising:

providing a transgenic plant containing a nucleic acid that includes:

an inducible transposable element including a first nucleotide sequence encoding a transposase, and a pathogenesis-related protein 1a promoter operably linked to the first nucleotide sequence;

an uncoupled promoter; and a second nucleotide sequence encoding a polypeptide, wherein, upon removal of the inducible transposable element during transposition, the uncoupled promoter becomes operably linked to the second nucleotide sequence;

contacting a flowering tissue of the transgenic plant with salicylic acid to thereby induce a transposition in a germ cell of the transgenic plant;

pollinating the germinal tissue of the transgenic plant;

and germinating seedlings from the germinal tissue to produce the progeny plant.

3. The method of claim 2, wherein the germinal tissue is contacted with an aqueous solution containing at least about 0.5 mM salicylic acid.

4. The method of claim 3, wherein the aqueous solution contains about 1 to 10 mM salicylic acid.

5. The method of claim 4, wherein the aqueous solution contains about 5 mM salicylic acid.

6. The method of claim 3, wherein the aqueous solution contains at least about 30 mM salicylic acid.

7. The method of claim 6, wherein the aqueous solution contains about 50 mM salicylic acid.

* * * * *